United States Patent
Causevic

(10) Patent No.: US 8,041,136 B2
(45) Date of Patent: Oct. 18, 2011

(54) SYSTEM AND METHOD FOR SIGNAL PROCESSING USING FRACTAL DIMENSION ANALYSIS

(75) Inventor: Elvir Causevic, New York, NY (US)

(73) Assignee: Brainscope Company, Inc., Bethesda, MD (US)

(*) Notice: Subject to any disclaimer, the term of this patent is extended or adjusted under 35 U.S.C. 154(b) by 849 days.

(21) Appl. No.: 12/106,699

(22) Filed: Apr. 21, 2008

(65) Prior Publication Data
US 2009/0263034 A1 Oct. 22, 2009

(51) Int. Cl.
*G06K 9/36* (2006.01)
*G06K 9/46* (2006.01)

(52) U.S. Cl. ........................ 382/249

(58) Field of Classification Search .......... 382/232, 382/233, 248–251, 254, 276, 295; 348/241
See application file for complete search history.

(56) References Cited

U.S. PATENT DOCUMENTS

| | | | |
|---|---|---|---|
| 5,065,447 A * | 11/1991 | Barnsley et al. | 382/249 |
| 5,848,198 A * | 12/1998 | Penn | 382/276 |
| 5,870,502 A * | 2/1999 | Bonneau et al. | 382/249 |
| 6,360,021 B1 * | 3/2002 | McCarthy et al. | 382/254 |
| 6,360,122 B1 | 3/2002 | Fischell et al. | |
| 6,654,623 B1 | 11/2003 | Kästle | |
| 7,054,453 B2 | 5/2006 | Causevic et al. | |
| 7,299,088 B1 | 11/2007 | Thakor et al. | |
| 7,302,064 B2 | 11/2007 | Causevic et al. | |
| 7,373,198 B2 | 5/2008 | Bibian et al. | |
| 7,904,144 B2 * | 3/2011 | Causevic et al. | 600/544 |
| 2002/0039455 A1 | 4/2002 | Kanamaru et al. | |
| 2002/0141652 A1 * | 10/2002 | Charrier et al. | 382/248 |
| 2004/0223656 A1 * | 11/2004 | Moreira | 382/240 |
| 2005/0207660 A1 * | 9/2005 | Edgar | 382/232 |
| 2006/0165307 A1 * | 7/2006 | Kondo et al. | 382/249 |
| 2006/0217632 A1 | 9/2006 | Causevic et al. | |
| 2007/0032737 A1 | 2/2007 | Causevic et al. | |
| 2007/0173732 A1 | 7/2007 | Causevic et al. | |
| 2009/0263034 A1 * | 10/2009 | Causevic | 382/249 |
| 2010/0191139 A1 * | 7/2010 | Jacquin et al. | 600/544 |
| 2011/0087125 A1 * | 4/2011 | Causevic | 600/544 |
| 2011/0112426 A1 * | 5/2011 | Causevic | 600/544 |

FOREIGN PATENT DOCUMENTS

WO WO 2006/034024 3/2006

OTHER PUBLICATIONS

Vorobyov et al., "Blind noise reduction for multisensory signals using ICA and subspace filtering, with application to EEG analysis," Biol. Cybern. 86, 293-303 (2002).

(Continued)

*Primary Examiner* — Amir Alavi
(74) *Attorney, Agent, or Firm* — Finnegan, Henderson, Farabow, Garrett & Dunner, L.L.P.

(57) ABSTRACT

A system and method of signal processing using linear or non-linear signal transformation and fractal dimension based analysis. Using a transform process (i.e. wavelet transform, Fourier transform, ICA transform, etc.), a signal is decomposed into a series of coefficients or components. Within this transform domain, fractal dimensions of the components are computed. The components with fractal dimensions higher than a pre-determined threshold are then selectively processed. A modified signal is reconstructed using inverse transform of the signal components.

14 Claims, 2 Drawing Sheets

OTHER PUBLICATIONS

Blakely, "A fast empirical mode decomposition technique for nonstationary nonlinear time series," Center for Scientific Computation and Mathematical Modeling, University of Maryland, College Park, Oct. 3, 2005.

Hadjileontiadis et al., "Empirical mode decomposition and fractal dimension filter," IEEE Engineering in Medicine and Biology Magazine, Jan./Feb. 2007, p. 30-39.

PCT Search Report and Written Opinion issued by European Patent Office in International Application No. PCT/US2009/041109, mailing date Jun. 8, 2009.

Comon, "Independent component analysis, A new concept?," *Signal Processing*, 36:287-314 (1994).

Delorme et al., "Enhanced detection of artifacts in EEG data using higher-order statistics and independent component analysis," *NeuroImage* 34:1443-1449 (2007).

Higuchi, "Approach to an Irregular Time Series on the Basis of the Fractal Theory," *Physica D* 31:277-283 (1988).

Hyvärinen, "Fast and robust fixed-point algorithms for independent component analysis," *IEEE Transactions on Neural Networks* 10(3):626-634 (1999).

Jung et al., "Removing electroencephalographic artifacts by blind source separation," *Psychophysiology* 37:163-178 (2000).

Ksiezyk et al., "Neural networks with wavelet preprocessing in EEG artifact recognition," Laboratory of Medical Physics, Institute of Experimental Physics, Warsaw University, Hoza 69 00 681 Warszawa, Poland, 1999.

U.S. Appl. No. 12/059,014, filed Mar. 31, 2008.

U.S. Appl. No. 12/041,106, filed Mar. 3, 2008.

\* cited by examiner

SYSTEM AND METHOD FOR SIGNAL PROCESSING USING FRACTAL DIMENSION ANALYSIS

FIELD OF THE INVENTION

This invention relates to the field of signal processing, and more particularly, to a method and system for automatic, real-time acquisition and processing of any signal.

BACKGROUND OF THE INVENTION

Fractal analysis, which provides a means for quantifying the complexity or degree of irregularity of any object or pattern, is a widely used analytical tool in a variety of research areas including physics, signal and image processing, acoustics, geophysics, biology, electrochemistry, and even sociology. In the field of image processing in particular, fractal analysis is used for various tasks, such as denoising, segmentation, estimation, compression, edge detection, classification, and synthesis, Computation of different fractal quantities, such as fractal dimensions, Holder exponents or multifractal spectra, provide improved indices for the analysis of irregular, but otherwise self-similar (scale-invariant) objects, also referred to as fractal objects, which cannot be represented with conventional Euclidean geometries.

Global measures of regularity are commonly used for applications such as classification or monitoring of fractal objects. The most well known measures of global regularity are fractal dimension estimates, defined either as regularization dimension, classical box-dimension or Hausdorff dimension. Fractal dimension D has become a widely accepted parameter for quantifying the complexity of feature details present in an object, and there are many methods and algorithms available for fractal dimension estimation of such geometries.

The fractal concept can also be extended to complex time-varying signals or processes that lack a single time scale in analogy to fractal geometries that lack a single length scale. Examples of time-varying signals include brain electrical signals, cardiac signals, output from chemical or electrical sensors in response to sensed parameters, radar signal, etc. Such time-varying signals generate irregular fluctuations across multiple time scales, and can be considered as fractal time-series. As similar to fractal objects, fractal time-series can be characterized by their fractal dimension D.

The use of fractal techniques to analyze temporal events has been previously demonstrated through conversion of the temporal signal into spatial patterns, as disclosed in U.S. Pat. No. 6,422,998 to Vo-Dinh et al. The disclosed method of Fractal Analysis with Space-Time (FAST) coordinate conversion is based on the concept that, when the temporal signal of a process is converted into a spatial pattern, the element of this spatial pattern can be characterized and analyzed by fractal geometry. However, this technique does not involve modification or restoration of the signal in the spatial domain based on the fractal dimension estimate, and reconstruction of the modified signal.

The present invention involves a novel approach of using fractal dimensions to characterize and modify time-varying signals, by coupling fractal dimension analysis with signal decomposition. The proposed method can be used for various signal processing tasks, such as denoising, separation, classification, monitoring, edge detection etc.

Signal decomposition techniques are commonly used to correct or remove signal contaminates. These techniques are based on the "unmixing" of the input signal into some number of underlying components using a source separation algorithm, followed by "remixing" only those components that would result in a "clean" signal by nullifying the weight of unwanted components. There are various algorithms available for signal decomposition based on wavelet transform, Fast Fourier Transform, Independent Component Analysis (ICA), etc. The components that generate artifacts are identified and set to zero in the transform domain, and the "clean" signal is reconstructed using an inverse transform. Such a technique using wavelet transform is disclosed in U.S. Patent Publication No. 2007/0032737 A1 (application Ser. No. 11/195,001), incorporated herein by reference in its entirety.

The recognition and cancellation of unwanted components after the signal decomposition is, however, a complicated and tedious task, and is often performed by a human expert. There is currently no known method of automatic characterization and modification of signals based on their transform coefficients. The current invention presents a technique for automatic, real-time processing of signals by combining the signal transform method with fractal dimension analysis for selective processing of unwanted coefficients.

SUMMARY OF THE INVENTION

It is a primary object of the invention to present a technique for automatic, real-time processing of signal without requiring individual manual adjustment. In an exemplary embodiment, this is achieved by using a fractal dimension-based analysis of the signal components. The input signal is at first deconstructed into its constitutive coefficients using a linear or non-linear signal transformation method, such as Fast Fourier Transform, Independent Component Analysis (ICA)-based transform, wavelet transform, diffusion wavelet transform etc. The fractal dimensions of the transform coefficients are then calculated, and the coefficients that have a fractal dimension higher than a threshold value are selectively removed or re-scaled. The remaining coefficients are then remixed using inverse signal transform to generate a modified signal, which is then forwarded to downstream signal analysis and/or information processing.

In accordance with an exemplary embodiment of the invention, there is provided a method of signal modification comprising the steps of signal transformation, identification of unwanted components using fractal dimension analysis, selective thresholding of the unwanted components, and signal reconstruction using an inverse signal transform.

In accordance with a further illustrative embodiment of the present invention, there is provided an apparatus for practicing the invention, which can be embodied in the form of a computer program code containing instructions, which can either be stored in a computer readable storage medium such as floppy disks, CD-ROMs, hard drives etc., or can be transmitted over the internet, such that, when the computer program code is loaded into and executed by an electronic device such as a computer, a microprocessor or a microcontroller, the device and its peripheral modules become an apparatus for practicing the invention.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

DESCRIPTION OF ILLUSTRATIVE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

Figure 1:
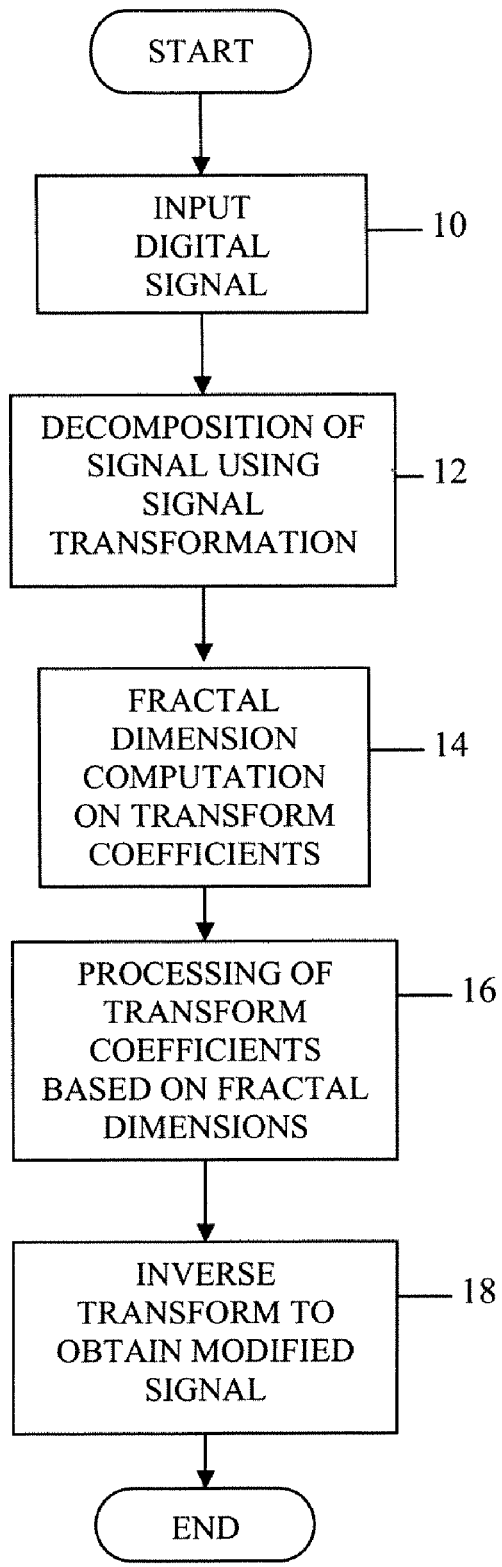
FIG. 1 is a flowchart illustrating the signal processing procedure carried out by a device according to an exemplary embodiment of the present invention.

In accordance with embodiments consistent with the present invention, FIG. 1 shows a flowchart illustrating a signal processing method. This method may be implemented by an electronic device, such as a computer or a microprocessor, which has the instructions for performing the method loaded into its internal memory. A digitized signal is entered into the signal processor (step 10). The signal is then decomposed into its coefficients or components using a signal transform (step 12). As shown in equation (1), X[n] is the transform of the signal x[n].

$$x[n] \xleftrightarrow{T} X[n] \quad (1)$$

In one embodiment, the signal is decomposed using a linear signal transform, such as a wavelet transform, Fourier transform, etc. In another embodiment, the signal may be decomposed using a non-linear transform, such as diffusion wavelet transform.

Referring again to FIG. 1, the fractal dimensions of the transform coefficients are then computed (step 14) using the algorithm proposed by Higuchi (T. Higuchi, *Physica D* 31, 1988, 277-238), which is incorporated herein by reference in its entirety. However, any other algorithm for estimating fractal dimensions may also be used. Unlike many estimates of the fractal dimension, the estimator proposed by Higuchi has the advantage of having low computational complexity, along with giving reliable estimates with as few as 100 data points.

Time-varying signals have Euclidean dimension of 1. But when they fluctuate non-periodically, they can have fractal dimensions spanning between Euclidean dimensions 1-2. If signal components with a fractal dimension lower than a certain threshold are desired, than all the transform coefficients with fractal dimensions higher than the preset threshold value are automatically canceled or re-scaled or otherwise selectively processed, and vice versa (step 16). This process of signal modification is a non-linear operation as different components are affected differently by the process. The signal is then reconstructed using inverse transform of the intact and re-scaled coefficients (step 18) to generate a modified signal. As shown in equation (2), the modified signal $x_d[n]$ is obtained as:

$$x_d[n] \xleftrightarrow{T^{-1}} QX[n] \quad (2)$$

where Q is a non-linear operator that processes one component $X_k[n]$ ($k^{th}$ component of X[n]) at a time in the transform domain.

This method of signal processing allows a user to work with fewer data points, and allows much faster acquisition and processing of data sets to be used for signal analysis. This is particular important for applications where immediate results are sought, as in the case of medical diagnostic signal processing in the emergency department or in an ambulatory setting.

Figure 2:
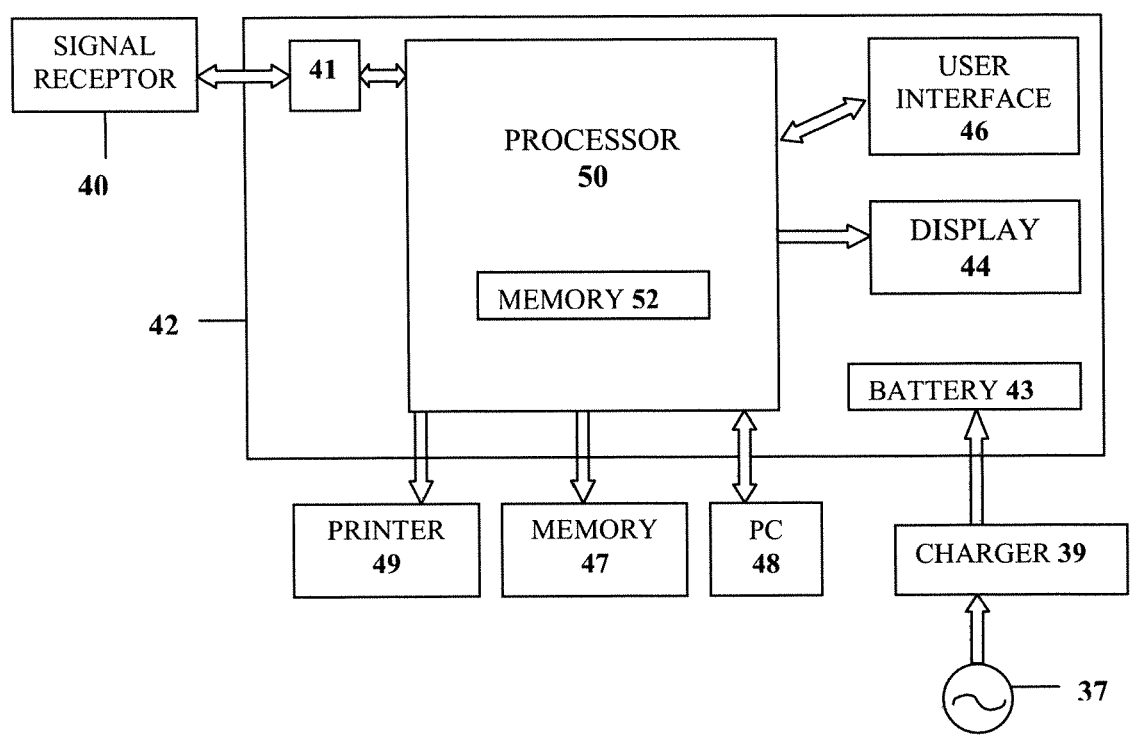
FIG. 2 is a diagram illustrating an apparatus according to an exemplary embodiment consistent with the present invention. The apparatus illustrated here incorporates a processor that is configured to perform the signal processing procedure illustrated in FIG. 1.

In accordance with embodiments consistent with the present invention, FIG. 2 shows a modular apparatus for practicing the invention. This modular apparatus consists of a first device, the signal acquisition unit 40, which interfaces with a signal source. The signal to be processed can be an acoustic signal, a biological signal such as electrical activity of the brain or heart, radar signal, etc. Accordingly, this signal acquisition unit 40 can be any receiving antenna, an electrode set placed on a subject's body for receiving bio-signals, etc. The signal acquisition unit 40 is connected to a handheld-device 42, which has a display 44, which can be a LCD screen, and can further have a user interface 46, which can be a touch screen user interface or a traditional key-board type interface. The handheld device 42 also contains analog and digital hardware on the front end 41, which is controlled by the processor 50, and may contain an ADC to convert analog signals to digital signals. The front end 41 can act as a multi-channel input/output interface for the device, to facilitate bidirectional communication of signals to and from the processor 50, such that a command from the user entered through the user interface 46 starts the signal acquisition process of unit 40. In one embodiment consistent with the present invention, the front end 41 is a wireless input/output interface, and the signal acquisition unit 40 and the front end 41 include wireless power amplifiers and RF transceivers.

In an embodiment consistent with the present invention, the signal processor 50, performs the signal modification procedure, as illustrated in FIG. 1, as per instructions loaded into its internal memory 52. The modified signal may be further processed in the processor 50 to extract signal features, and the output maybe displayed on the display 44, or maybe saved in external memory 47, or maybe displayed on the PC 48 connected to the handheld device 42.

In one embodiment consistent with the present invention, the display 44 is external to the handheld device module, and the results from the processor 50 are transmitted wirelessly to the external display, or to the external memory 47. The handheld device module, in this embodiment, further comprises a wireless power amplifier coupled to an antenna to transmit the results wirelessly. In yet another embodiment, the results are transmitted wirelessly to a printer 49 that prints the results.

Handheld device 42 also contains an internal rechargeable battery 43 that can be charged during or in between uses through charger 39 connected to AC outlet 37. The battery can also be charged wirelessly through electromagnetic coupling by methods known in the prior art, in which case the handheld device 42 would also contain an antenna for receiving the RF emission from an external source.

In another embodiment consistent with the present invention, the processor 50 transmits the raw, unprocessed signal to the computer 48. The computer performs the signal processing method illustrated in FIG. 1, further analyzes the signal and output the results.

In one embodiment, the signal acquisition unit 40 and the handheld device 42 along with the charger 39 may come as a kit for field use or point-of-care applications.

In one embodiment consistent with the present invention, the signal acquisition unit 40 is connected to a subject's body to acquire biological signals, such as brain electrical signals or cardiac signals, and it transmits the acquired signal wirelessly to the device 42. In yet another embodiment consistent with the present invention, the signal acquisition unit 40, the front end 41 and the processor 50 are connected to the subject's body, and the output results are transmitted wireless to the PC 48. The unit 40, the front end 41 and the processor 50, in this case, are configured to reside in a single portable unit.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for processing an acquired signal, comprising the steps of:
   providing a signal acquisition device configured to interface with one or more signal sources;
   providing a signal processing device operatively connected to the signal acquisition device, the signal processing device comprising a processor configured to perform the steps of:
   i. transforming the signal into a plurality of signal coefficients;
   ii. computing fractal dimension of the coefficients;
   iii. identifying unwanted coefficients based on their fractal dimension;
   iv. automatically thresholding the identified unwanted coefficients;
   v. reconstructing a modified signal using inverse transform.

2. The method as recited in claim 1, wherein the step of signal transformation is linear.

3. The method as recited in claim 1, wherein the step of signal transformation is non-linear.

4. The method as recited in claim 1, wherein the step of identifying unwanted components is performed automatically and requires no user intervention.

5. The method as recited in claim 1, wherein the step of automatic thresholding is performed on signal coefficients having a fractal dimension higher or lower than a threshold value.

6. The method as recited in claim 5, wherein the threshold value is predetermined.

7. The method as recited in claim 5, wherein the thresholding is a non-linear process.

8. The method as recited in claim 5, wherein the thresholding comprises removing or re-scaling the signal coefficients having a fractal dimension higher or lower than the threshold value.

9. The method of claim 8, wherein the step of reconstructing a modified signal is performed using inverse transform of intact coefficients and the re-scaled coefficients.

10. The method as recited in claim 1, further comprising the step of automatically forwarding the modified signal for further signal analysis.

11. A system for signal processing, the system comprising:
    means for acquiring signals from one or more signal sources;
    means for transmitting the acquired signals for signal processing;
    means for signal transformation to deconstruct the signal into its coefficients;
    means for computing the fractal dimension of the coefficients;
    means for automatically thresholding the coefficients with fractal dimensions higher or lower than a predetermined threshold value; and
    means for reconstructing a modified signal using inverse transform of intact and threshold coefficients.

12. The system as recited in claim 11, wherein the means for signal transformation is linear.

13. The system as recited in claim 11, wherein the means for signal transformation is non-linear.

14. The system as recited in claim 11, wherein the means for signal removing or re-scaling the coefficients with fractal dimensions higher or lower than the predetermined threshold value.

* * * * *